(12) United States Patent
Heywang et al.

(10) Patent No.: US 6,440,401 B1
(45) Date of Patent: Aug. 27, 2002

(54) 2-PHENYL-BENZIMIDAZOLESULFONIC ACIDS AS UV-B FILTERS

(75) Inventors: Ulrich Heywang, Darmstadt; Michael Schwarz, Weiterstadt; Frank Pflücker, Darmstadt, all of (DE)

(73) Assignee: Merck Patent Gesellschaft Mit Beschraenkter Haftung (DE)

( * ) Notice: Subject to any disclaimer, the term of this patent is extended or adjusted under 35 U.S.C. 154(b) by 0 days.

(21) Appl. No.: 09/989,172

(22) Filed: Nov. 21, 2001

Related U.S. Application Data

(63) Continuation of application No. 09/885,967, filed on Jun. 22, 2001, now abandoned.

(30) Foreign Application Priority Data

Jun. 23, 2000 (DE) .......................................... 100 30 663

(51) Int. Cl.[7] ...................... A61K 31/4184; A61K 7/42; C07D 235/18
(52) U.S. Cl. .................. 424/59; 548/310.1; 548/310.7; 514/395; 514/60
(58) Field of Search ........................... 548/310.1, 310.7; 514/395; 424/59, 60

(56) References Cited

U.S. PATENT DOCUMENTS

| 2,104,492 A | 1/1938 | Merkel et al. |
| 5,473,079 A | 12/1995 | Heywang et al. |
| 5,585,091 A | 12/1996 | Pelzer et al. |
| 6,248,311 B1 | 6/2001 | Candau |

FOREIGN PATENT DOCUMENTS

| DE | 676103 | 5/1939 |
| DE | 19923712 A1 | 5/1999 |
| DE | 19923773 A1 | 5/1999 |
| EP | 669323 A1 | 8/1995 |
| EP | 868904 A2 | 7/1998 |
| EP | 1027881 A1 | 8/2000 |
| WO | 9315061 | 8/1993 |

OTHER PUBLICATIONS

Derwent WPI english language abstract of DE 19923712 A1, 2000.
Derwent WPI english language abstract of DE 19923773, 2000.
Derwent WPI english language abstract of EP 868904, 1998.
Derwent WPI english language abstract of EP 669323, 1995.
Derwent WPI english language abstract of EP 1027881, 2000.
Derwent WPI english language abstract of WO 9315061, 1993.

*Primary Examiner*—Laura L. Stockton
(74) *Attorney, Agent, or Firm*—Millen, White, Zelano & Branigan, P.C.

(57) ABSTRACT

Disclosed is a 2-phenyl-benzimidazolesulfonic acid according to the formula

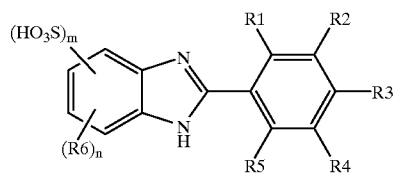

I in which
n is 0, 1 or 2 and
m is 2 or 3,
R1, R2, R3, R4 and R5, are each a radical such as H, $C_{1-8}$-alkyl, $C_{1-8}$-alkoxy, hydroxyl, sulfate, nitro, F, Cl, Br or I radicals, and
R6 is a $C_{1-8}$-alkyl or $C_{1-8}$-alkoxy radical.

This compound can be effectively used as a UV filter, and as part of a cosmetic formulation which comprise these compounds. A process for preparation of the compound is disclosed as well.

25 Claims, No Drawings

2-PHENYL-BENZIMIDAZOLESULFONIC ACIDS AS UV-B FILTERS

This application is a copending continuing application from prior copending application Ser. No. 09/885,967, filed Jun. 22, 2001, now abandoned.

The present invention relates to a 2-phenyl-benzimidazolesulfonic acids, to the use thereof as a UV filter, to cosmetic preparations which comprise these compounds, and to a preparation process for the compounds.

A suntan of the skin to whatever degree is regarded in today's society as attractive and as an expression of vigor and health. As well as this desired effect of the sun on the skin, however, a number of undesired secondary effects arise, such as sunburn or premature skin aging and the development of wrinkles. A number of performance UV filters have been developed which, applied to the skin in the form of creams, lotions or gels, can effectively delay the development of sunburn even when the incidence of solar rays is relatively high.

The UV filter present in the pharmaceutical or cosmetic formulation forms a film or a layer on the surface of the skin and does not penetrate into deeper skin layers with other substances present in the formulation. Known UV filters or sun protection agents thus act only by absorbing certain regions of sunlight; meaning that this radiation cannot penetrate into deeper layers of the skin.

As is known, the most hazardous part of solar radiation is formed by the ultraviolet rays having a wavelength of less than 400 nm. The lower limit of the ultraviolet rays which reach the surface of the earth is limited by the absorption in the ozone layer to about 280 nm or above. The sun protection filters which are currently customary in cosmetics absorb in a wavelength range from 280 to 400 nm. This range includes UV-B rays having a wavelength between 280 and 320 nm, which play a decisive role in the formation of a solar erythema, and UV-A rays, having a wavelength between 320 and 400 nm, which tan the skin but also age it, and favor the triggering of an erythematous reaction or can exacerbate this reaction in certain people or even trigger phototoxic or photoallergic and irritative reactions.

The object of skin care cosmetics is to obtain the impression of a youthful skin. In principle, there are various ways of achieving this object. For example, existing skin damage, such as irregular pigmentation or the development of wrinkles can be smoothed out by covering powders or creams. Another approach is to protect the skin against environmental influences which lead to permanent damage and thus aging of the skin.

The idea is therefore to intervene in a preventative manner and thus to delay the aging process. One example of this is the UV filters already mentioned which, as a result of absorption of certain wavelength regions, prevent or at least reduce skin damage. Depending on the position of their absorption maxima, UV absorbers for cosmetic and dermatological preparations are divided into UV-A and UV-B absorbers. UV-A absorbers usually also absorb in the UV-B region and are thus alternatively referred to as broad-band absorbers or broad-band filters. However, particularly in avoiding skin damage as a result of the formation of solar erythemas, the UV-B filters are of particular importance, since formulations based on broad-band filters alone offer inadequate protection or prevent entirely the desired tanning of the skin. For this reason, there is a continuous need for substances having an absorption maximum in the UV-B region which can be incorporated easily into cosmetic formulations.

Of decisive importance for the formulation is the solubility of the filter substances in the oil and water phases since it is necessary, particularly for establishing a high protection factor, to incorporate filters into all phases of a formulation. The oil-soluble UV-B filters include isooctyl methoxycinnamate, isoamyl methoxycinnamate and methylbenzylidenecamphor. Examples of water-soluble UV filters are, in particular, the salts of 2-phenylbenzimidazole-5-sulfonic acid, the use of which as UV ray filter has already been described in German Reichspatent No. 676 103.

However, a disadvantage of these water-soluble UV-B filters is that formulation is only possible in an alkaline medium since the sulfonic acid precipitates out at a pH below 7.

There is thus also a need for water-soluble UV-B filters which are highly suitable for the formulation of cosmetic formulations.

It has now surprisingly been found that certain 2-phenylbenzimidazolesulfonic acids and salts thereof can be readily incorporated into cosmetic formulations, while avoiding the above-mentioned problems.

The present invention accordingly firstly provides 2-phenylbenzimidazolesulfonic acids of the formula I

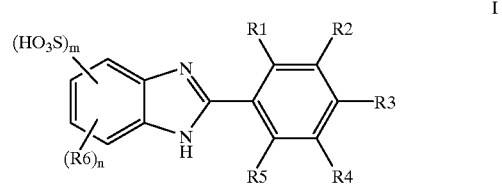

in which n is 0, 1 or 2 and m is 2 or 3. R1, R2, R3, R4 and R5 are each a radical from the group H, $C_{1-8}$-alkyl, $C_{1-8}$-alkoxy, hydroxyl, sulfate, nitro, F, Cl, Br or I radicals, and $R_6$ is a $C_{1-8}$-alkyl or $C_{1-8}$-alkoxy radical.

For the purposes of the present invention, 2-phenyl-benzimidazolesulfonic acids are here in principle also understood as meaning the salts of these acids. The salts are preferably the alkali metal salts, and in particular the sodium or potassium salts, or the ammonium salts, in particular the triethanolammonium salts of the corresponding sulfonic acids.

In a preferred 2-phenylbenzimidazolesulfonic acid according to formula I, m=2 and n=0 or n=1, preferably at least 4 radicals from the group R1, R2, R3, R4 and R5 are H, and particularly preferably even all radicals R1–R5 are H. According to the invention, particular preference is accordingly given to 2-phenylbenzimidiazole-4,6-disulfonic acid which, as shown in formula Ia, is usually in betaine form.

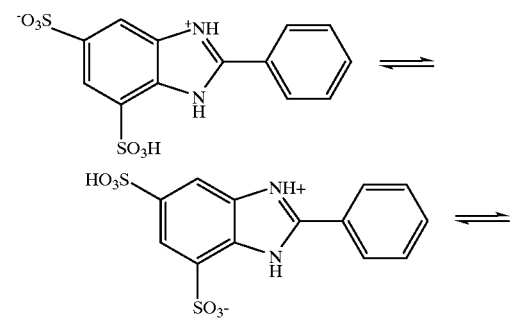

-continued

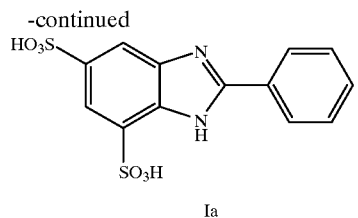

Ia

The 2-phenylbenzimidazolesulfonic acid according to the invention can be obtained by any desired preparation process suitable for this purpose. Processes which have proven particularly suitable and economical are those in which an ortho-phenylenediamine or a derivative thereof is reacted with an arylcarboxylic acid or an arylcarboxylic acid derivative.

The present invention thus secondly provides a process for the preparation of the abovedescribed 2-phenylbenzimidazolesulfonic acids, in which an o-phenylenediamine according to formula II

II is reacted with a second compound according to formula III

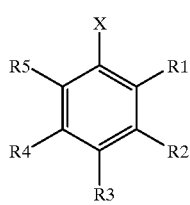

III where R1, R2, R3, R4 and R5, in each case independently of one another, are a radical from the group of H, $C_{1-8}$-alkyl, $C_{1-8}$-alkoxy, hydroxyl, nitro, F, Cl, Br or I radicals, and X is chosen from the radicals —COOH, —COCl, —COBr, —CN or —COOR, where R is a $C_{1-20}$-alkyl radical.

In a preferred embodiment of the process, sulfuric acid, in particular 96% sulfuric acid, is used as solvent. Here, even the sulfuric acid on its own effects sulfonation of the benzimidazole at a suitable temperature. Thus, international application WO 93/15061 has already described a process in which monosulfonated products are obtained by reaction in sulfuric acid.

However, in the process for the preparation of polysulfonated benzimidazoles, it is preferred if an activated sulfuric acid is used, activation preferably being carried out by chlorosulfonic acid or sulfur trioxide. Sulfuric acid alone typically is not strong enough to act as a reagent for this process because it is believed that water forms during the reaction and dilutes the sulfuric acid. Activation of the acid improved the reactivity of the acid in the process.

The use of chlorosulfonic acid for the preparation of bisbenzimidazoloylsulfonic acids has already been described in European patent application EP-A-669 323. However, there are no indications that it is also possible to use chlorosulfonic acid to prepare the compounds according to the invention in the specification.

If the activation is carried out using sulfur trioxide, use is preferably made of the "fuming" sulfuric acid called oleum, which is a solution of sulfur trioxide in concentrated sulfuric acid. The use of sulfur trioxide (oleum) for the activation of the sulfuric acid has various advantages compared with the use of chlorosulfonic acid:

gas (HCl) is not evolved during the reaction, meaning that pressure regulation is not necessary, accordingly, the collection and disposal of the aggressive gas (HCl) is not required, while extremely corrosion-resistant apparatuses are required for the chloride-containing sulfuric acid which is formed if chlorosulfonic acid is used, the process with oleum can be carried out in less complex equipment, after hydrolysis of the oleum, sulfuric acid is present which can be recycled, with relative ease while the recycling of the chloride-containing sulfuric acid resulting from the use of chlorosulfonic acid is only possible with difficulty.

As a result of these advantages, it is preferred according to the present invention to activate the sulfuric acid using sulfur trioxide (oleum).

If the process according to the invention is carried out with activated sulfuric acid, then it is preferred that X in the second compound of formula III is a radical —COOH, i.e., that formula III is an arylcarboxylic acid. In another likewise preferred embodiment of the process, X in formula III is a radical —COOR, where R is a $C_{1-20}$-alkyl radical, preferably a $C_{1-8}$-alkyl radical and particularly preferably a methyl or ethyl radical.

Here, it is particularly preferred that the reaction is carried out at temperatures between 20° C. and 200° C., preferably between 160° C. and 190° C. The reaction temperature is usually maintained for 2 to 8 hours. At reaction times of less than 2 hours, monosulfonation products are still observed, which can only be separated off from the product with difficulty.

Implementation of the process according to the invention is in itself straightforward for one skilled in the art. A preferred embodiment for carrying out the reaction is given below. This may serve as an example, but does not limit the possible embodiments for carrying out the reaction:

The sulfuric acid, preferably in the form of a 50–100% solution, and in particular as a concentrated approximately 96% solution, is introduced. The orthophenylenediamine, or derivative thereof, is introduced. Activation with oleum (e.g. a 65% solution of sulfur trioxide in sulfuric acid) is then carried out at a temperature preferably below 150° C. The amount of sulfur trioxide is chosen such that all of the water liberated during the reaction can be collected. For example, for the preparation of a benzimidazoledisulfonic acid, at least 4 mol of sulfur trioxide are used per mole of o-phenylenediamine.

The addition of the second reactant (arylcarboxylic acid or arylcarboxylic acid derivative) is preferably only carried out for safety reasons after cooling to a temperature below 100° C. since the temperature of the reaction mixture may increase further as the result of the addition. The arylcarboxylic acid is expediently used in the ratio 1:1 to the phenylenediamine to obtain products according to the invention.

The reaction mixture is slowly heated to temperatures between 150 and 250° C., preferably between 160 and 200° C. and maintained at this temperature for 2 to 8 hours, optionally with stirring. The reaction mixture is then cooled, preferably to temperatures below 10° C., and hydrolyzed in water.

After the mixture has been stirred briefly, preferably 20 minutes to 2 hours, the solid constituents are separated off, preferably washed with warm water and dried.

To purify the dried crude product, it is preferably dissolved in sodium hydroxide solution, and the resulting solution is purified, preferably with activated carbon. The end-product is precipitated out of the colorless solution using an acid, preferably a mineral acid; for example sulphuric acid.

Because of its absorption maxima in the UV-B region, the 2-phenylbenzimidazolesulfonic acid according to the invention is suitable as a UV-B filter substance. Accordingly, the present invention further provides for the use of a 2-phenylbenzimidazolesulfonic acid as a UV filter, in particular as a UV-B filter.

Because of this use option, the substances according to the invention are highly suitable for use in cosmetic formulations. The invention thus further relates to cosmetic formulations having UV protection properties which comprise at least one compound of formula I according to the invention.

The protective action of these formulations against UV radiation can be improved if the formulation comprises one or more additional UV filter substances in addition to the UV filter according to the invention.

In principle, it appears that all UV filters are suitable for combination with the filter substance herein. Particular preference is given to combination with those UV filters whose physiological safety has already been demonstrated. There are many tried and tested substances known from the specialist literature both for UVA and also UVB filters, such as:

benzylidenecamphor derivatives, such as 3-(4'-methylbenzylidene)-dl-camphor (e.g. Eusolex® 6300), 3-benzylidenecamphor (e.g. Mexoryl® SD), polymers of N-{(2 and 4)-[(2-oxoborn-3-ylidene)-methyl]benzyl}acrylamide (e.g. Mexoryl® SW), N,N,N,-trimethyl-4-(2-oxoborn-3-ylidenemethyl)-anilinium methylsulfate (e.g. Mexoryl ® SK) or α-(2-oxoborn-3-ylidene)toluene-4-sulfonic acid (e.g. Mexoryl® SL), benzoylmethanes or dibenzoylmethanes, such as 1-(4-tert-butylphenyl)-3-(4-methoxyphenyl)propane-1,3-dione (e.g. Eusolex® 9020) or 4-isopropyldibenzoylmethane, benzophenones, such as 2-hydroxy-4-methoxy-benzophenone (e.g. Eusolex® 4360) or 2-hydroxy-4-methoxybenzophenone-5-sulfonic acid and its sodium salt (e.g. Uvinul® MS-40), methoxycinnamic esters, such as octyl methoxycinnamate (e.g. Eusolex® 2292), isopentyl 4-methoxycinnamate, e.g. as a mixture of the isomers (e.g. Neo Heliopan® E 1000), salicylate derivatives, such as 2-ethylhexyl salicylate (e.g. Eusolex® OS), 4-isopropylbenzyl salicylate (e.g. Megasol®) or 3,3,5-trimethyl-cyclohexyl salicylate (e.g. Eusolex® HMS), 4-aminobenzoic acid and derivatives, such as 4-aminobenzoic acid, 2-ethylhexyl 4-(dimethyl-amino) benzoate (e.g. Eusolex® 6007), ethoxylated ethyl 4-aminobenzoate (e.g. Uvinul® P25), benzimidazole derivatives, such as 2-phenylbenzimidazole-5-sulfonic acid, and its potassium, sodium, lithium, ammonium and triethanolamine salts (e.g. Eusolex® 232), 2,2'-(1,4-phenylene) bis(1H-benzimidazole-4,6-disulfonic acid, monosodium salt) (CAS No. 180 898-37-7) and 2,2'-(1,4-phenylene)bis(1H-benzimidazole-5-sulfonic acid) and its potassium, sodium and triethanolamine salts and further substances, such as 2-ethylhexyl 2-cyano-3, 3-diphenylacrylate (e.g. Eusolex® OCR), 3,3-(1,4-phenylenedimethylene)bis(7,7-dimethyl-2-oxobicyclo-[2.2.1]hept-1-ylmethanesulfonic acid, and its salts (e.g. Mexoryl® SX), 2,4,6-trianilino-(p-carbo-2'-ethylhexyl-1'-oxy)-1,3,5-triazine (e.g. Uvinul® T 150), 2-(2H-benzo-triazole-2-yl)-4-methyl-6-(2-methyl-3-(1,3,3,3-tetramethyl-1-(trimethylsilyloxy)disiloxanyl)-propyl)phenol (e.g. Silatriazole®), 4,4'-[(6-[4-((1,1,-dimethylethyl)aminocarbonyl)phenylamino]-1,3,5-triazine-2,4-diyl)diimino]bis(benzoic acid 2-ethylhexyl ester) (e.g. Uvasorb® HEB), α-trimethylsilyl)-ω-[trimethylsilyl)oxy]poly[oxy-(dimethyl [and approximately 6% methyl[2–8 p-[2,2-bis (ethoxycarbonyl) vinyl]phenoxy]-1-methylene-ethyl] and about 1.5% methyl[3–8 p-2,2-bis(ethoxy-carbonyl) vinyl)phenoxy) propenyl) and 0.1 to 0.4% (methylhydrogen)silylene]] (n≈60) (CAS No. 207 574-74-1), 2,2'-methylenebis(6-(2H-benzotriazole-2-yl) -4-(1,1,3,3-tetramethylbutyl) phenol) (CAS No. 103 597-45-1) and 2,4-bis{[4-(2-ethylhexyloxy)-2-hydroxy]phenyl}-6-(4-methoxyphenyl)-1,3,5-triazine (CAS No. 103 597-45-[lacuna], 187 393-00-6).

The compounds given in the list are only to be regarded as examples. It is of course also possible to use other UV filters. These organic UV filters are, and the 2-phenylbenzimidazolesulfonic acids according to the invention, are typically each incorporated into cosmetic formulations in an amount of from 0.5 to 20% by weight of the formulation, preferably in an amount of 1–15% by weight and particularly preferably in an amount of from 2 to 8% by weight per individual substance. Overall, the organic filters usually comprise up to 40% by weight, preferably 5 to 25% by weight, of the formulation, which includes the filter substance of the invention and any additional organic filter substances.

Inorganic UV filters such as those from the group of titanium dioxides, such as, for example, coated titanium dioxide (e.g. Eusolex® T-2000, Eusolex® T-AQUA), zinc oxides (e.g. Sachtotec®), iron oxides and also cerium oxides can also be combined. These inorganic UV filters are usually incorporated into cosmetic formulations in an amount of from 0.5 to 20 per cent by weight of the overall formulation, preferably 2–10%.

If various inorganic or organic UV filters are used, then these can be used in virtually any ratios relative to one another. The ratios of the individual substances to one another are usually in the range 1:10–10:1, preferably in the range 1:5–5:1 and particularly preferably in the range 1:2–2:1. If UV-A filters are used in addition to UV-B filters, then it is advantageous for most applications if the proportion of UV-B filters predominates and the ratio of UV-A filters:UV-B filters is preferably in the range 1:1 to 1:3.

Preferred filter compounds for combination with the 2-phenylbenzimidazolesulfonic acids according to the invention, preferred compounds having UV-filtering properties for the cosmetic preparations are 3-(4'-methylbenzylidene) -dl-camphor, 1-(4-tert-butylphenyl)-3-(4-methoxyphenyl)propane-1,3-dione, 4-isopropyldibenzoylmethane, 2-hydroxy-4-methoxybenzo-phenone, octyl methoxycinnamate, 3,3,5-trimethyl-cyclohexyl salicylate, 2-ethylhexyl 4-(dimethyl-amino) benzoate, 2-ethylhexyl 2-cyano-3,3-diphenyl-acrylate, coated titanium dioxide and in particular 2-phenylbenzimidazole-5-sulfonic acid and 2,2'-(1,4-phenylene) bis(1H-benzimidazole-5-sulfonic acid) and its potassium, sodium, lithium, ammoniium and triethanolamine salts.

The protecting action against oxidative stress or against the effect of free radicals can be further improved if the formulation comprises one or more antioxidants.

There are many tried and tested substances known from the specialist literature which can be used as an antioxidant in the formulation such as amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glycerylesters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine-sulfoximine, homocysteine-sulfoximine, buthionine-sulfone, penta-, hexa- and heptathionine-sulfoximine) in very low tolerated doses (e.g. pmol to µmol/kg), and also (metal) chelating agents, (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate), and coniferyl benzoate of benzoin resin, rutin and salts of the sulfuric ester of rutin and derivatives thereof, α-glycosyl rutin, ferulic acid, furfurylidineglucitol, carosine, butylhydroxy-toluene, butylhydroxyanisol, nordihydroguaretic acid, trihydroxybutyrophenone, quercetin, uric acid and derivatives thereof, mannose and derivatives thereof, zinc and derivatives thereof (e.g. ZnO, $ZnSO_4$), selenium and derivatives thereof (e.g. selenomethionine), and stilbenes and derivatives thereof (e.g. stilbene oxide, trans-stilbene oxide).

Mixtures of antioxidants are likewise suitable for use in the cosmetic formulations according to the invention. Known and commercial mixtures are, for example, mixtures comprising, as active ingredients, lecithin, L-(+)-ascorbyl palmitate and citric acid (e.g. Oxynex® AP), natural tocopherols, L-(+)-ascorbyl palmitate, L-(+)-ascorbic acid and citric acid (e.g. Oxynex® K LIQUID), tocopherol extracts from natural sources, L-(+)-ascorbyl palmitate, L-(+)-ascorbic acid and citric acid (e.g. Oxynex® L LIQUID), DL-α-tocopherol, L-(+)-ascorbyl palmitate, citric acid and lecithin (e.g. Oxynex® LM) or butylhydroxytoluene (BHT), L-(+)-ascorbyl palmitate and citric acid (e.g. Oxynex® 2004).

The formulations according to the invention can also comprise vitamins as ingredients. Preferably, the vitamins used are vitamins and vitamin derivatives chosen from vitamin A, vitamin A propionate, vitamin A palmitate, vitamin A acetate, retinol, vitamin B, thiamine chloride hydrochloride (vitamin $B_1$), riboflavin (vitamin $B_2$), vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$) nicotinic acid (niacin), pyridoxine, pyridoxal, pyridoaxmine, (vitamin $B_6$), panthothenic acid, biotin, folic acid and cobalamine (vitamin $B_{12}$) are present in the cosmetic formulations according to the invention, particularly preferably vitamin A palmitate, vitamin C, DL-α-tocopherol, tocopherol E acetate, nicotinic acid, panthothenic acid and biotin.

The compound according to the invention can be incorporated into cosmetic formulations in the customary manner. Suitable formulations are those for external use, such as cream, lotion, gel or as a solution which can be sprayed onto the skin. In this respect, it is preferred if the preparation comprises at least one oil phase and at least one water phase, and that the 2-phenylbenzimidazolesulfonic acid according to the invention is present in at least one aqueous phase.

The cosmetic or pharmaceutical formulations according to the invention can take a number of terms, such as: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Any customary carriers, auxiliaries and optionally further active ingredients may be added to the formulation.

Preferred auxiliaries originate from the group of preservatives, antioxidants, stabilizers, solubility promoters, vitamins, colorants, odour improvers.

Ointments, pastes, creams and gels may comprise the customary carriers, e.g. animal and vegetable fats, waxes, paraffins, starch, tragacanth, cellulose derivatives, polyethylene glycols, silicones, bentonites, silica, talc and zinc oxide or mixtures of these substances.

Powders and sprays may comprise the customary carriers, e.g. lactose, talc, silica, aluminium hydroxide, calcium silicate and polyamide powder or mixtures of these substances. Sprays can additionally comprise customary propellants, e.g. chlorofluorocarbons, propane/butane or dimethyl ether.

Solutions and emulsions can comprise the customary carriers, such as solvents, solubility promoters and emulsifiers, e.g. water, ethanol, isopropanol, ethyl carbonate, ethyl acetate, benzyl alcohol, benzyl benzoate, propylene glycol, 1,3-butylglycol, oils, in particular cotton seed oil, peanut oil, wheatgerm oil, olive oil, castor oil and sesame oil, glycerol fatty acid ester, polyethylene glycols and fatty acid esters of sorbitan or mixtures of these substances.

Suspensions can comprise the customary carriers such as liquid diluents, e.g. water, ethanol or propylene glycol, suspending agents, e.g. ethoxylated isostearyl alcohols, polyoxyethylene sorbitol esters and polyoxyethylene sorbitan esters, microcrystalline cellulose, aluminium metahydroxide, bentonite, agar and tragacanth or mixtures of these substances.

Soaps can comprise the customary carriers, such as alkali metal salts of fatty acids, salts of fatty acid mono esters, fatty acid protein hydrolysates, isethionates, lanolin, fatty alcohol, vegetable oils, plant extracts, glycerol, sugars or mixtures of these substances.

Surfactant-containing cleansing products can comprise the customary carrier substances, such as salts of fatty alcohol sulfates, fatty alcohol ether sulfates, sulfosuccinic monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters or mixtures of these substances.

Face and body oils can comprise the customary carrier substances such as synthetic oils, such as fatty acid esters, fatty alcohols, silicone oils, natural oils, such as vegetable oils and oily plant extracts, paraffin oils, lanolin oils or mixtures of these substances.

Cosmetic application forms also typical forms such as lipsticks, lip care sticks, mascara, eyeliner, eye shadow, blusher, powder makeup, emulsion make-up and wax make-up, and such protection products such as sunscreen, pre-sun and after-sun preparations.

All compounds or components which can be used in the cosmetic formulations are either known and available commercially or can be synthesized by known processes.

The cosmetic formulation according to the invention is particularly suitable for protecting human skin against the harmful influences of the UV constituents in sunlight. It can also offer protection to the skin against aging processes of the skin and against oxidative stress, i.e. against damage caused by free radicals, as are produced, for example, by solar irradiation, heat or other influences. In this connection, it is in various forms customarily used for this application. For example, the formulation may be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The formulation may comprise cosmetic auxiliaries which are customarily used in this type of preparation, such as thickeners, softeners, moisturizers, surface-active agents, emulsifiers, preservatives, antifoams, perfumes, waxes, lanolin, propellants, dyes and/or pigments which color the composition itself or the skin, and other ingredients customarily used in cosmetics.

It is possible to use an oil, wax or other fatty substance, a lower monoalcohol or a lower polyol or mixtures thereof as a dispersant or solubilizer. Preferred monoalcohols or polyols include ethanol, isopropanol, propylene glycol, glycerol and sorbitol.

A preferred embodiment of the invention is an emulsion in the form of a protective cream or milk and which, apart from the 2-phenylbenzimidazolesulfonic acid(s) according to the invention and preferably further UV filters, comprise, for example, fatty alcohols, fatty acids, fatty acid esters, in particular triglycerides of fatty acids, lanolin, natural and synthetic oils or waxes and emulsifiers in the presence of water.

Further preferred embodiments include oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The cosmetic preparation according to the invention can also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes are usually used.

The cosmetic formulation can also be used to protect the hair against photochemical damage in order to prevent changes of color shades, decoloration or damage of a mechanical nature. In this case, a suitable formulation is in the form of a shampoo, lotion, gel or emulsion for rinsing out, the formulation in question being applied before or after shampooing, before or after coloring or bleaching or before or after permanent waving. It is also possible to choose a formulation in the form of a lotion or gel for styling or treating the hair, in the form of a lotion or gel for brushing or blow-waving, in the form of a hair lacquer, permanent waving composition, colorant or bleach for the hair. Apart from the 2-phenyl-benzimidazolesulfonic acid(s) according to the invention and further UV filters, the cosmetic formulation may comprise various adjuvants used in this type of composition, such as surface-active agents, thickeners, polymers, softeners, preservatives, foam stabilizers, electrolytes, organic solvents, silicone derivatives, oils, waxes, antigrease agents, dyes and/or pigments which color the composition itself or the hair, or other ingredients customarily used for hair care.

The cosmetic preparations according to the invention can be prepared using techniques which are well known to the person skilled in the art.

To protect the skin and/or natural or sensitized hair against solar rays, a cosmetic preparation comprising the compound of the invention is applied to the skin or the hair. Sensitized hair is understood here as meaning hair which has been subjected to a chemical treatment, such as a permanent waving treatment, a coloring process or bleaching process.

In addition, the compound of the invention also has a stabilizing effect on the formulation. When used in corresponding products, the formulations are thus also stable for longer and do not change their appearance. In particular, even in the case of longer-lasting application or relatively long storage, the effectiveness of the ingredients, e.g. vitamins, is retained. This is particularly advantageous in the case of compositions for protecting the skin against the effect of UV rays since these cosmetics are exposed to particularly high stresses by UV radiation.

The invention further provides for the stabilization of particular UV filters. A known high-performance class of light protection filter substances is formed by the dibenzoyl-methane derivatives. However, a disadvantage is that these substances are very readily decomposed by UV light and thus their protecting properties are lost. An example of a light protection filter from this compound class which is available commercially is 4-(tert-butyl)-4'-methoxydibenzoylmethane, which has the structure given in formula IV.

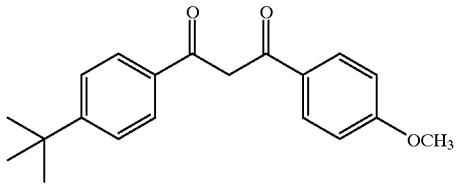

IV

Surprisingly, it has now been found that the compound of the invention has a very good stabilizing action for the dibenzoylmethanes, in particular 4-(tert-butyl)-4-Methoxydibenzoylmethane. By incorporating mixtures of these compounds into cosmetics, it is now possible to prepare light protection compositions using dibenzoyl-methanes which show no or only a low decrease in the protective action against UV rays, even in the case of a relatively long period of solar action, for example during sunbathing for a number of hours.

The entire disclosure of all applications, patents and publications, cited above and below, and of corresponding German Application No. 100 30 663.2, filed Jun. 23, 2000 is hereby incorporated by reference.

The examples below illustrate the present invention in more detail.

In the foregoing and in the following examples, all temperatures are set forth uncorrected in degrees Celsium; and, unless otherwise indicated, all parts and percentages are by weight.

Antaron® V-220 is sold by GAF, Frechen, DE,
Carbomer Ultrez-10 is supplied by Goodrich, Neuss, DE,
Dehymuls® E is a mixture of dicocoylpentaerythritol citrate, sorbitol sesquioleate, beeswax and aluminium stearate and is sold by Cogni, Roermond, NL,
Eusolex® 2292, Eusolex 232, Eusolex® 6300 and Eusolex® HMS are UV filters sold by Merck KGaA, Darmstadt, DE,
Luvitol® EHO is sold by BASF AG, Ludwigshafen, DE,
Pemulen® TR-1 and Pemulen® TR-2 are acrylate/alkyl acrylate polymers sold by Goodrich, Neuss, DE,
Performa® V825 is a synthetic wax sold by New Phase, NJ08554, US,
Oxynex K is a mixture of PEG-8, tocopherol, ascorbyl palmitate, ascorbic acid and citric acid and is sold by Merck KGaA, Darmstadt, DE.

EXAMPLE 1
Preparation of 2-phenylbenzimidazole-4,6-disulfonic acid 108 parts of o-phenylenediamine are introduced into 500 parts of $H_2SO_4$ (>96%) and then 800 parts of oleum (65%) are added dropwise, the temperature being maintained at a maximum of 120° C. After 15 min, the mixture is cooled to 70° C. and 120 parts of benzoic acid are added. The mixture is heated for 2 h at 180° C. The mixture is slowly hydrolysed with 2 500 parts of water, the temperature being maintained below 10° C. The precipitate (crystals) is filtered off with suction, the crude product is suspended in 8 parts of water and dissolved with 32% sodium hydroxide solution at pH=7. The solution is stirred with activated carbon until colorless, and thereafter precipitation is induced using 96% $H_2SO_4$ by establishing a pH=1–2. 300 parts of 2-phenylbenzimidazole-4,6-disulfonic acid are obtained. The compound has an absorption maximum in the UV-B region at $\lambda_{max=308}$ nm.

The following are prepared analogously:
2-(4'-methoxyphenyl)benzimidazole-4,6-disulfonic acid
2-(3'-methoxyphenyl)benzimidazole-4,6-disulfonic acid
2-(4'-ethoxyphenyl)benzimidazole-4,6-disulfonic acid
2-(3'-ethoxyphenyl)benzimidazole-4,6-disulfonic acid
2-(3'-5'-dimethoxyphenyl)benzimidazole-4,6-disulfonic acid
2-(3'-5'-diethoxyphenyl)benzimidazole-4,6-disulfonic acid
2-(3'-4'-diethoxyphenyl)benzimidazole-4,6-disulfonic acid.

EXAMPLE 2
Sunscreen Spray (O/W)

| Phase | Ingredient | % by wt. |
|---|---|---|
| A | Eusolex ® 2292 (Art No. 105382) | 7.50 |
|   | Eusolex ® HMS (Art. No. 111412) | 7.00 |
|   | Steareth-2 | 0.40 |
|   | Steareth-10 | 0.80 |
|   | Pemulen ® TR-2 | 0.18 |
|   | Propylene glycol isoceteth-3 acetate | 5.00 |
|   | Performa ® V 825 | 0.80 |
|   | Dimethicone | 1.00 |
|   | Oxynex ® K (Art. No. 108324) | 0.10 |
| B | 2-Phenylbenzimidazole-4,6-disulfonic acid | 1.00 |
|   | Triethanolamine | 0.90 |
|   | 1,2-Propanediol | 2.00 |
|   | Preservative | 0.50 |
|   | Water, demineralised | ad 100.00 |

Preparation:
Phase B: The water is mixed with the triethanolamine and the 2-phenylbenzimidazole-4,6-disulfonic acid is added with stirring. As soon as everything has dissolved, the other constituents of Phase B are added and the mixture is heated to 80° C.

Phase A: The constituents of Phase A, with the exception of Pemulen® TR-2, are combined and heated to 80° C. The Pemulen®TR-2 is added with stirring.

Preparation of the sunscreen composition: Phase B is slowly added with stirring to Phase A. Following homogenization, the mixture is cooled with stirring. The preservatives used are 0.05% of propyl 4-hydroxybenzoate and 0.15% of methyl 4-hydroxybenzoate.

EXAMPLE 3
Sunscreen Spray (O/W)

| Phase | Ingredient | % by wt. |
|---|---|---|
| A | Eusolex ® 2292 (Art No. 105382) | 7.50 |
|   | Eusolex ® HMS (Art. No. 111412) | 7.00 |
|   | Steareth-2 | 0.40 |
|   | Steareth-10 | 0.80 |
|   | Pemulen ® TR-2 | 0.18 |
|   | Propylene glycol isoceteth-3 acetate | 5.00 |
|   | Performa ® V 825 | 0.80 |
|   | Dimethicone | 1.00 |
|   | Oxynex ® K (Art. No. 108324) | 0.10 |
| B | 2-Phenylbenzimidazole-4,6-disulfonic acid | 1.00 |
|   | Eusolex ® 232 (Art No. 105372) | 1.00 |
|   | Triethanolamine | 0.90 |
|   | 1,2-Propanediol | 2.00 |
|   | Water, demineralized | ad 100.00 |

Preparation:
Phase B: The water is mixed with the triethanolamine and Eusolex®232 and the 2-phenylbenzimidazole-4,6-disulfonic acid are added with stirring. As soon as everything has dissolved, the other constituents of Phase B are added and the mixture is heated to 80° C.

Phase A: The constituents of Phase A, with the exception of Pemulen® TR-2, are combined and heated to 80° C. The Pemulen® TR-2 is added with stirring.

Preparation of the sunscreen composition: Phase B is slowly added with stirring to Phase A. After homogenization, the mixture is cooled with stirring. The preservatives used are 0.05% of propyl 4-hydroxy-benzoate and 0.15% of methyl 4-hydroxybenzoate.

EXAMPLE 4
Sunscreen Gel (aqueous)

| Phase | Ingredient | % by wt. |
|---|---|---|
| A | 2-Phenylbenzimidazole-4,6-disulfonic acid | 1.00 |
|   | Eusolex ® 232 (Art. No. 105372) | 4.00 |
|   | Sodium hydroxide solution | 6.00 |
|   | Glycerol | 3.00 |
|   | 1,2-Propanediol | 2.00 |
|   | Preservative | q.s. |
|   | Water, demineralized | ad 100.00 |
| B | Carbomer Ultrez-10 | 0.70 |
|   | Water, demineralized | 60.00 |
| C | Sodium hydroxide solution (10%) | 1.50 |
|   | Water, demineralized | 4.00 |

Preparation:
Carbomer Ultrez-10 is completely dispersed in the water of Phase B. Phase C is then slowly added and the mixture is homogenized.

For Phase A, the water is first added to the sodium hydroxide solution. The Eusolex® 232 is added and completely dissolved with stirring. After a clear solution has been obtained, the other constituents of Phase A are added.

Phase A is added in portions to the mixture of Phases B and C, the mixture being homogenized after each addition.

The preservative used is:

0.20% of methyl 4-hydroxybenzoate

EXAMPLE 5

Sunscreen Gel (O/W)

| Phase | Ingredient | % by wt. |
|---|---|---|
| A | Eusolex ® 6300 (Art No. 5385) | 0.75 |
|   | Luvitol ® EHO | 10.00 |
|   | Dimethicone | 2.00 |
|   | Shea butter | 5.00 |
|   | Antaron ® V-220 | 2.00 |
|   | Oxynex ® K | 1.00 |
| B | 2-Phenylbenzimidazole-4,6-disulfonic acid | 1.00 |
|   | Eusolex ® 232 (Art No. 105372) | 0.75 |
|   | Tris(hydroxymethyl)aminomethane | 0.33 |
|   | Preservative | q.s. |
|   | Water, demineralized | 20.00 |
| C | Tris(hydroxymethyl)aminomethane | 1.20 |
|   | Water, demineralized | 10.00 |
| D | Pemulen ® TR-1 | 0.60 |
|   | Water, demineralized | ad 100.00 |

Preparation:

The Pemulen® TR-1 is dissolved in the water of Phase D. The tris(hydroxymethyl)aminomethane is dissolved in the water of Phase C and the solution is added to Phase D. The tris(hydroxymethyl)aminomethane is dissolved in the water of Phase B and, with stirring, the Eusolex® 232 is added. After a clear solution has been obtained, the other constituents of Phase B are added and Phase B is added to the mixture of Phases C and D and homogenized. The constituents of Phase A are combined and heated. Phase D is added to the mixture of the other phases with homogenization.

The preservatives used are 0.05% of propyl 4-hydroxybenzoate and 0.15% of methyl 4-hydroxybenzoate.

EXAMPLE 6

Sunscreen Gel (O/W)

| Phase | Ingredient | % by wt. |
|---|---|---|
| A | Eusolex ® 6300 (Art No. 5385) | 0.75 |
|   | Luvitol ® EHO | 10.00 |
|   | Dimethicone | 2.00 |
|   | Shea butter | 5.00 |
|   | Antaron ® V-220 | 2.00 |
|   | Oxynex ® K liquid (Art. No. 8324) | 1.00 |
| B | 2-Phenylbenzimidazole-4,6-disulfonic acid) | 1.00 |
|   | 2,2'-(1,4-Phenylene)bis(1H-benzimidazole-4,6-disulfonic acid | 0.75 |
|   | Tris(hydroxymethyl)aminomethane | 0.33 |
|   | Preservative | q.s. |
|   | Water, demineralized | 20.00 |
| C | Tris(hydroxymethyl)aminomethane | 1.20 |
|   | Water, demineralized | 10.00 |
| D | Pemulen ® TR-1 | 0.60 |
|   | Water, demineralized | ad 100.00 |

Preparation:

The Pemulen® TR-1 is dissolved in the water of Phase D.

The tris(hydroxymethyl)aminomethane is dissolved in the water of Phase C and the solution is added to Phase D.

The tris(hydroxymethyl)aminomethane is dissolved in the water of Phase B and the 2-phenylbenzimidazole-4,6-disulfonic acid and the 2,2'-(1,4-phenylene)bis(1H-benzimidazole-4,6-disulfonic acid) is added with stirring. After a clear solution has been obtained, the other constituents of Phase B are added, and Phase B is added to the mixture of Phases C and D and homogenized. The constituents of Phase A are combined and heated. Phase A is added to the mixture of the other phases with homogenization.

The preservatives used are 0.05% of propyl 4-hydroxybenzoate and 0.15% of methyl 4-hydroxybenzoate.

EXAMPLE 7

Sunscreen Lotion (W/O) With UVA/B Protection

| Phase | Ingredient | % by wt. |
|---|---|---|
| A | Eusolex ® 2292 (Art. No. 105382) | 3.00 |
|   | Eusolex ® 4360 (Art. No. 105376) | 2.00 |
|   | Dehymuls ® E | 6.00 |
|   | Hydrogenated castor oil | 1.00 |
|   | Beeswax | 2.00 |
|   | Oleyl erucate | 6.00 |
|   | Decyl oleate | 6.00 |
|   | Dimethicone | 1.00 |
|   | Dicapryl ether | 5.00 |
| B | Glycerol (87%) | 5.00 |
|   | 2-Phenylbenzimidazole-4,6-disulfonic acid | 3.00 |
|   | Magnesium sulfate heptahydrate | 1.00 |
|   | Preservative | q.s. |
|   | Water, demineralized | ad 100.00 |

Preparation:

The constituents of Phases A and B are each combined. Phase A is heated to 75° C. and Phase B is heated separately to 80° C. Phase B is added to Phase A with homogenization. The mixture is cooled with stirring.

The preservatives used are:

0.05% of propyl 4-hydroxybenzoate 0.15% of methyl 4-hydroxybenzoate.

EXAMPLE 8

Sunscreen Lotion (W/O) With UVA/B Protection

| Phase | Ingredient | % by wt. |
|---|---|---|
| A | Eusolex ® 2292 (Art. No. 105382) | 3.00 |
|   | Eusolex ® 4360 (Art. No. 105376) | 2.00 |
|   | Dehymuls ® E | 6.00 |
|   | Hydrogenated castor oil | 1.00 |
|   | Beeswax | 2.00 |
|   | Oleyl erucate | 6.00 |
|   | Decyl oleate | 6.00 |
|   | Dimethicone | 1.00 |
|   | Dicapryl ether | 5.00 |
| B | 2-Phenylbenzimidazole-4,6-disulfonic acid | 2.00 |
|   | 2,2'-(1,4-Phenylene)bis(1H-benzimidazole-5-sulfonic acid) | 2.00 |
|   | Glycrol (87%) | 5.00 |
|   | Magnesium sulfate heptahydrate | 1.00 |
|   | Preservative | q.s. |
|   | Water, demineralized | ad 100.00 |

Preparation:

The constituents of Phases A and B are each combined. Phase A is heated to 75° C. and, separately, Phase B is heated to 80° C. Phase B is added to Phase A with homogenization. The mixture is cooled with stirring.

The preservatives used are:

0.05% of propyl 4-hydroxybenzoate 0.15% of methyl 4-hydroxybenzoate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Patent claims

1. A 2-Phenylbenzimidazolesulfonic acid according to the formula I

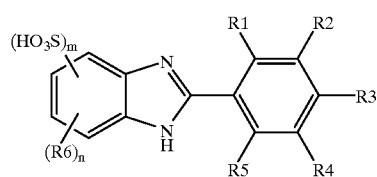

wherein n is 0–2 and m is 2–3,

R1, R2, R3, R4 and R5 each are a radical selected from H, $C_{1-8}$-alkyl, $C_{1-8}$-alkoxy, hydroxyl, sulfate, nitro, F, Cl, Br and an I radical, and R6 is a $C_{1-8}$-alkyl or $C_{1-8}$-alkoxy radical.

2. A 2-Phenylbenzimidazolesulfonic acid according to claim 1, wherein m=2 and n=0–1, and wherein at least 4 radicals from the group R1, R2, R3, R4 and R5 are H radicals.

3. A process for the preparation of a compound according to claim 1, wherein an o-phenylenediamine according to formula II

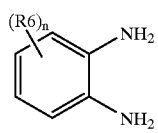

is reacted with a compound according to the formula III

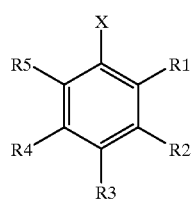

wherein R1, R2, R3, R4 and R5, are each, independently of one another, a radical selected from H, $C_{1-8}$-alkyl, $C_{1-8}$-alkoxy, hydroxyl, sulfate, nitro, F, Cl, Br and an I radical, and wherein X is a radical selected from —COOH, —COCl, —COBr, —CN and —COOR, and wherein R is a $C_{1-20}$-alkyl radical.

4. A method according to claim 3, wherein the reaction is carried out in sulfuric acid.

5. A UV filter substance comprised of a 2-phenylbenzimidazolesulfonic acid according to claim 1.

6. A cosmetic formulation having UV protection properties comprising at least one filter substance comprised of at least one 2-phenyl-benzimidazolesulfonic acid according to claim 1.

7. A cosmetic formulation according to claim 6, wherein the formulation comprises at least one oil phase and at least one water phase, and wherein the 2-phenylbenzimidazolesulfonic acid is present in the at least one water phase.

8. A cosmetic formulation according to claim 6, further comprising at least one additional UV filter substance, wherein each filter substance is present in the formulation in an amount of from 0.5 to 20% by weight of the entire formulation.

9. A cosmetic formulation according to claim 6, further comprising at least one of the following compounds 3-(4'-methylbenzylidene)-dl-camphor, 1-(4-tert-butylphenyl) -3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate coated titanium dioxide, 2-phenylbenzimidazole-5-sulfonic acid and 2,2'-(1,4-phenylene) bis(1H-benzimidazole-5-sulfonic acid).

10. A stabilizing substance for a UV filter comprising a 2-phenylbenzimidazolesulfonic acid according to claim 1.

11. A method according to claim 3, wherein the radicals R1–R5 are each an H radical.

12. A method according to claim 3, wherein R is a $C_{1-8}$ alkyl radical.

13. A method according to claim 4, wherein the sulphuric acid is activated sulphuric acid.

14. A method according to claim 4, wherein the reaction is carried out at a temperature of 160° C. to 190° C.

15. A method according to claim 13, further comprising activating the sulphuric acid using chlorosulfonic acid or oleum.

16. A method according to claim 13, further comprising activating the sulphuric acid using oleum.

17. A UV filter substance according to claim 5, wherein the UV filter substance further comprises a UV-B filter substance.

18. A formulation according to claim 8, wherein the filter substance is a UV-A filter substance.

19. A formulation according to claim 8, wherein each filter substance is present in the formulation in an amount from 1 to 15% by weight of the entire formulation.

20. A formulation according to claim 8, wherein each filter substance is presence in the formulation in an amount from 2 to 8% by weight of the entire formulation.

21. A formulation according to claim 8, wherein the filter substances together comprise from 5 to 25% by weight of the entire formulation.

22. A formulation according to claim 6, further comprising 2-phenylbenzimidazole-5-sulfonic acid and/or 2,2'-(1,4-phenylene)bis(1H-benzimidazole-5-sulfonic acid).

23. A substance according to claim 10, wherein the UV filter is dibenzoylmethane or a derivative of dibenzoylmethane.

24. A formulation according to claim 6, further comprising at least one antioxidant.

25. A formulation according to claim 6, further comprising at least one vitamin.

* * * * *